United States Patent [19]

Samis

[11] E Re. 30,594

[45] Reissued Apr. 28, 1981

[54] POSITIVE IDENTIFICATION METHOD AND STRUCTURE

[76] Inventor: Philip L. Samis, 4400 St. Catherine St. W., Apt. 606, Westmount, Quebec, Canada

[21] Appl. No.: 46,254

[22] Filed: Jun. 7, 1979

Related U.S. Patent Documents

Reissue of:

[64] Patent No.: 4,027,391
Issued: Jun. 7, 1977
Appl. No.: 560,616
Filed: Mar. 21, 1975

[30] Foreign Application Priority Data

Mar. 26, 1974 [GB] United Kingdom ..... 13353/74

[51] Int. Cl.[3] ..... A61C 5/00
[52] U.S. Cl. ..... 433/229
[58] Field of Search ..... 433/226, 228, 203, 229; 40/2.2 R; 119/3, 1; 128/1 R, 92 C; 283/7, 8 A, 8 R, 9 R; 63/1 R

[56] References Cited

U.S. PATENT DOCUMENTS

| | | | |
|---|---|---|---|
| 1,182,254 | 5/1916 | Cummins | 63/1 R |
| 1,275,669 | 8/1918 | Forbes | 171/112 |
| 1,744,043 | 1/1930 | Grant | 633/203 |
| 2,029,553 | 2/1936 | Bartschi et al. | 36/1 |
| 2,650,588 | 9/1953 | Drew | 128/92 |
| 2,939,958 | 7/1960 | Andersson | 250/67 |
| 3,128,744 | 4/1964 | Jefferts et al. | 119/3 |
| 3,571,957 | 3/1971 | Cummings | 40/2.2 |
| 3,573,455 | 4/1961 | Suierveld | 250/65 |
| 3,600,807 | 8/1971 | Sipos | 32/2 |
| 3,643,358 | 2/1972 | Morderosian | 40/2.2 |
| 3,788,276 | 8/1972 | Propst et al. | 119/1 |
| 3,805,301 | 4/1974 | Liebig | 3/1 |
| 3,921,318 | 11/1975 | Calavetta | 283/7 |
| 4,056,952 | 11/1977 | Okuda | 40/2.2 |

FOREIGN PATENT DOCUMENTS

| | | | |
|---|---|---|---|
| 62236 | 3/1944 | Denmark | 250/476 |
| 1566325 | 1/1968 | France | 128/1 R |

OTHER PUBLICATIONS

"Radiopague Tags Can Reveal Ingested Drugs," Medical World News, 6(45): pp. 132–133, Dec. 3, 1965.

*Primary Examiner*—Robert Peshock
*Attorney, Agent, or Firm*—Robert E. Mitchell; Arthur Schwartz

[57] ABSTRACT

The present invention relates to a method to assist in the identification of a living body which comprises selecting a carrier, transcribing information as to the identity of the body on the carrier, and fixing the carrier to a hard mineralized portion of the body. The structure includes a miniaturized carrier of relatively inert material and having identifying intelligence thereon, wherein the carrier is adapted to be fixed or otherwise embedded on hard mineralized tissue of the body.

27 Claims, 11 Drawing Figures

POSITIVE IDENTIFICATION METHOD AND STRUCTURE

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a method and structure for positive identification of humans or animals, and more particularly to an intelligence bearing article adapted to be securely and retrievably stored in a living body for subsequent or post-mortem identification of the body of the human or animal.

2. Description of the Prior Art

Recent airline disasters have resulted in a large number of human victims whose visual identification was impossible. Also, it has been found very difficult, if not impossible, in many cases to identify with any degree of certainty the decomposing bodies of victims of drowning or multilated bodies of victims of crimes.

Reference is made to "Handbook for Dental Identification, Techniques in Forensic Dentistry", by Lester L. Luntz, D.D.S. and Phyllys Luntz; J. B. Lippincott Company, Philadelphia and Toronto, 1973, for a comprehensive treatise on the subject.

It has been found in air disasters, particularly, wherein intense heat has been experienced over a short period of time, that although the body flesh may be considerably deteriorated, such as by burning, the flesh does act as an insulation which protects highly mineralized hard tissues such as a bone or teeth. Teeth are relatively non-destructible but are almost totally incinerated at 1250° F. Reliance is increasingly placed on methods of identification of victims involving an examination of their teeth and thereby correlating the remains with their dental records, resulting in the specialized science of forensic odontology. It is evident from a review of the literature that there is a need for a better method, than the present understandardized system, to achieve a higher degree of certainty in the post-mortem identification of such visually unidentifiable victims by the forensic odontologist, pathologist and police authority.

Under such circumstances and in view of the increasing mobility of humans and animals in the modern way of life, as well as the increasing use of incendiary weapons in modern warfare, there is obviously a need for a method by which a dead person or animal could be identified rapidly and with a high degree of certainty.

SUMMARY OF THE INVENTION

It is an aim of the present invention to provide a method of positive identification of the body of a person or animal, which method would be simple and widely available without the necessity of setting up centralized or separate records and be subject to relatively less sophisticated forensic investigation procedures than is now required. It is also an aim of the present invention to provide an identification structure compatible with the method of identification. It is a further aim of the present invention to provide a method and structure for positive identification which would be easily applied by dentists, for instance, in the normal course of dental restoration done on their patients. Most people living in countries where frequent dental monitoring is carried out, as a matter of course, would at least have been exposed to the availability of the identification method.

It is an aim of the present invention to provide a carrier on which the name and other identification characteristics of a person might be inscribed or otherwise etched on the carrier and then embedded in a tooth which, in the case of necessity, could be retrieved and be read by a microscope or simple magnifying glass.

A method in accordance with the present invention comprises the steps of selecting a carrier of relatively inert material providing identifying intelligence on said carrier, selecting a predetermined, relatively inert portion of a living body, and fixing the intelligence bearing carrier to said selected part of the body.

In a more specific embodiment, the method could, in application to human beings, include the steps of selecting a carrier of miniaturized dimensions and locating the miniaturized intelligence bearing carrier on a tooth or in a cavity formed in a tooth in the normal course of dental restoration. It is also within the scope of the method of this invention to fix the intelligence bearing carrier to a suitable location on a bone of the body or in a cavity made in the bone.

In a structure in accordance with the present invention, there is provided a carrier of relatively inert material, bearing identifying intelligence thereon, fixed to a relatively hard and inert mineralized tissue of a living body and adapted to be recovered for subsequent identification purposes in living or post-mortem conditions.

In a more specific embodiment of a structure in accordance with the present invention, there is provided a combination of a relatively hard mineralized tissue portion of a body, said tissue portion being relatively accessible, an intelligence bearing carrier embedded in said mineralized tissue portion and said carrier being at least as inert as the mineralized tissue portion in which the carrier is embedded.

It is a further feature of the present invention to provide a locating means for assisting in the location of said intelligence bearing carrier when it is required to retrieve said carrier for identification purposes of the body wherein said locating means is at least radiographically opaque and has a predetermined detectable shape.

In a more specific embodiment, the carrier could have at least one surface sufficiently flat on which the identifying indicia could be placed. The carrier as a whole might be of any suitable shape and preferably of a shape capable of internal placement in a cavity in a tooth or bone. It may in some cases be in or under a restoration in a tooth and the surface receiving the identifying indicia may vary in some cases between 1.1 $mm^2$ and 2.5 $mm^2$, more preferably between 1.7 or 1.25 $mm^2$ and 2.0 $mm^2$. The maximum thickness would in such an embodiment be determined by the depth in the cavity and the minimum thickness will vary according to manufacturing techniques but presently would be between 0.250 and 1.270 mm. The carrier could, for example, be made of inert heat-resisting materials, such as ceramic or porcelain material, or a short length of metallic ribbon, such as stainless steel, tantalum or other nonoxidizing metal, such as gold, silver, alloys thereof, or the like.

It is important that the carrier being used be relatively inert such that no noticeable chemical reaction would occur while the carrier is embedded in the tooth or bone and that it have a melting point of at least that of the tooth or other mineralized tissue in which the carrier is embedded. It may be necessary in certain cases to provide a locating device such as an anchor pin, such as used in dental restoration which would be coded or shaped so as to distinguish it from an anchor pin and locate radiographically the area in which the carrier might be located. The locating pin should also be relatively inert and have a melting point of at least that of teeth or other mineralized tissue in which it may be located. It should also be radioactively opaque.

The carrier and locating means should be miniaturized, and the identification information should be somehow inscribed on the miniature carrier so that the small carrier can be located conveniently underneath a restoration in a tooth or embedded in a bone.

The back side of the carrier can be colour coded to serve as an indication to the operator excavating the restoration that he has reached his target and to minimize possible destruction of part of the identification carrier.

Certain features can also be built into the carrier, such as corrugating the edges in such a way to appear in X-rays as a definite feature of those tabs.

If the carrier is to be used flush with the surface of a tooth or bone, it should be coated with a protective coating, such as a transparent shellac resin coating, in order to protect the inscribed surface.

BRIEF DESCRIPTION OF THE DRAWINGS

Having thus generally described the invention, reference will now be made to the accompanying drawings, showing by way of illustration, preferred embodiments thereof, and in which.

DESCRIPTION OF THE PREFERRED EMBODIMENTS

Figure 1:
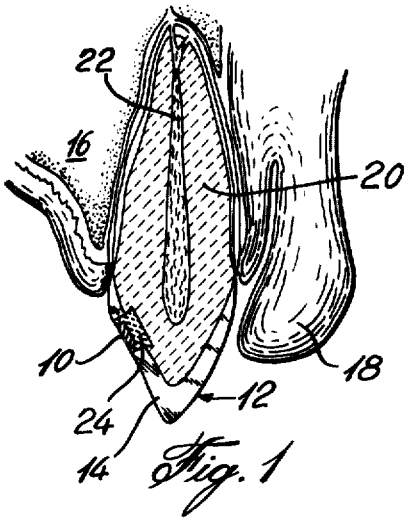
FIG. 1 is a vertical cross-section taken through a typical anterior tooth showing a detail of an embodiment of the present invention.
Figure 2:
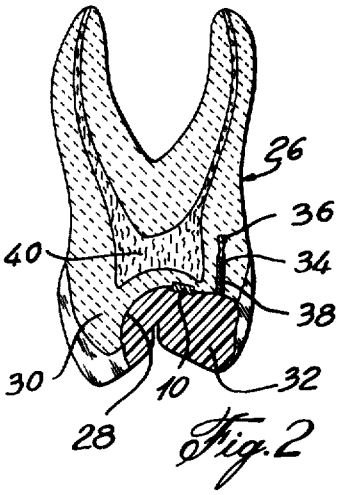
FIG. 2 is a vertical cross-section taken through a typical posterior tooth showing a detail of another embodiment of the structure.
Figure 3:
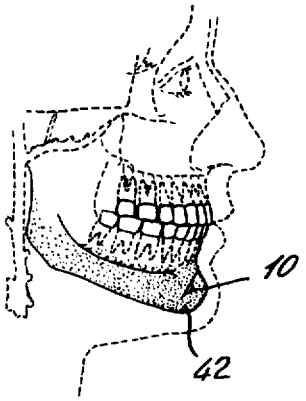
FIG. 3 is a partial side elevation of a typical mandible showing a detail of a third embodiment of the structure.

By way of example, the method and structure will now be referred to in the drawings, specifically in relation to the embodiments shown in FIGS. 1 to 3. FIGS. 1 to 3 show three examples of possible locations of a carrier 10. Referring to FIG. 1, a miniaturized identification plaque or carrier 10 may be placed so that it is flush with a surface of an anterior tooth 12 and specifically in an enameled crown 14 of the anterior tooth 12. In the drawing, numeral 16 represents the bone forming the socket of a tooth 12, while 18 represents the upper lip. The tooth 12 includes the dentin portion 20, and there is shown centrally thereof the pulp chamber and channel 22. In order to place the carrier 10 in the location shown in FIG. 1, an anchoring cavity may be formed in the crown 14 extending into the dentin 20, and a cement material 24 placed therein will adhere to the walls of the cavity as well as to the carrier 10 as it is located on the cement flush with the surface of the crown.

Referring to the embodiment shown in FIG. 2, a posterior tooth 26 is illustrated wherein a recess 28 has been formed through the enameled cusp into the dentin portion and has been filled with amalgam in the normal course of restoring the tooth. However, before filling the so-formed recess 28 with the amalgam 32, an identification carrier 10 was located face down in the bottom of the recess 28. In order that the location of the carrier 10 be more readily detected by radiographic procedures, a pin 34 which has a coded shaped terminal end 36 is provided in a sub-recess 38 communicating with a recess 28. The locating pin 34 should be located where a metallic type amalgam is used in restoring the teeth which might prevent the radiographic observation or detection of the carrier 10. The pin 36 is located such that it extends away from the mass of amalgam, but care is taken to avoid penetrating the pulp chamber 40 of the tooth 26.

It is considered also suitable to locate the identification carrier 10 in a suitable bone location of the living body. In the embodiment shown in FIG. 3, the carrier 10 is located in the mandible bone in the general area of the teeth such that an X-ray photograph of the teeth and mandible 42 will indicate the location of the rather square prismatic shape of a typical carrier 10.

Figure 4:
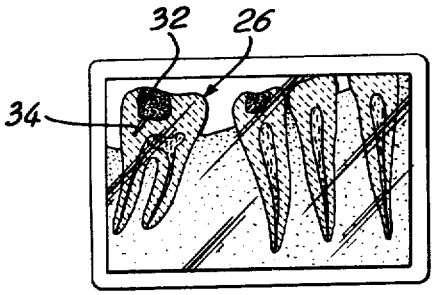
FIG. 4 is an illustration of a typical radiographic representation of teeth having the structure of the present invention.

FIG. 4 illustrates how a radiographic representation of a person's teeth could detect, by means of the pin 34, the tooth in which the identification carrier 10 is located.

Figure 6:
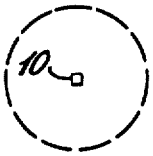
FIG. 6 is a top plan view of the actual size of the carrier.
Figure 7:
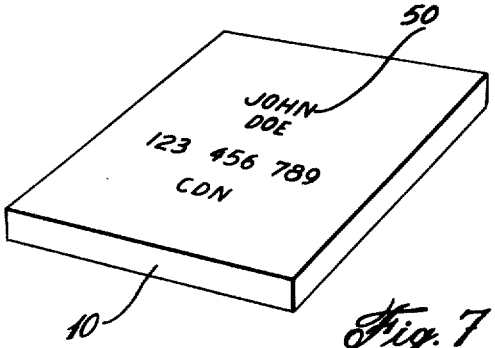
FIG. 7 is an enlarged perspective view of the carrier of FIG. 6.

A preferred carrier 10 is shown in FIGS. 6 and 7, including a ceramic substrate 43 made of, for instance, Beryllia (BeO) or Alumina ($Al_2O_3$). The carrier 10 is 0.6 mm. thick and is a square prism of 1.5 mm. square. A base metallic layer 44 of ni-chrome steel was vacuum-deposited on the ceramic substrate 43 and then a layer of gold 46 was vacuum-deposited on the ni-chrome layer. The identification includes the name of the individual, social insurance number, and citizenship, and was etched on the gold layer 46 and the ni-chrome layer 44 as will be described.

Figure 10:
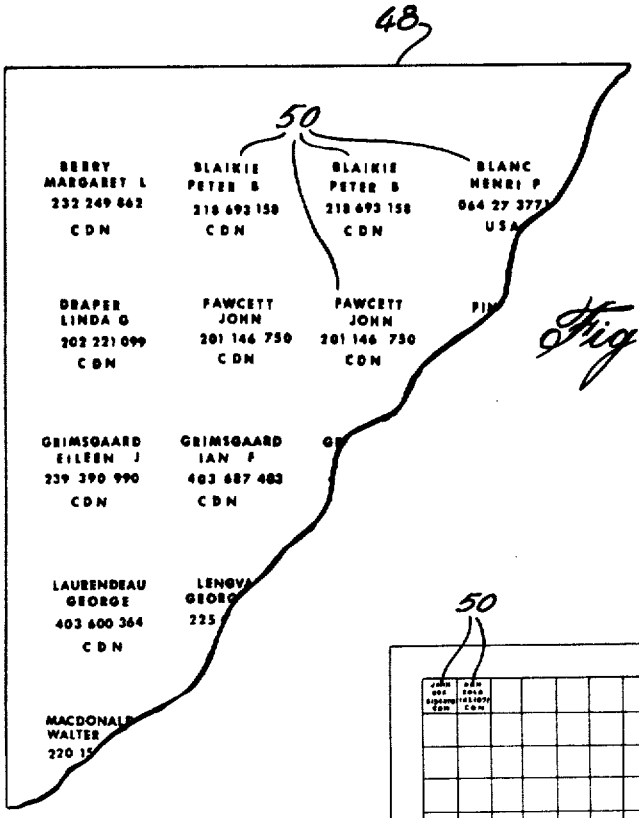
FIG. 10 is a fragmentary plan view of a detail of a step in the method of the present invention.
Figure 11:
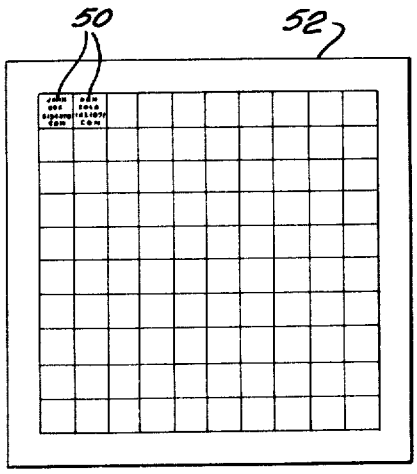
FIG. 11 is an enlarged view of a further detail of a step in the method of the present invention.

In a preferred process of preparing the miniaturized carrier having the identification etched thereon, the following steps were followed. Referring to FIG. 10, a master sheet 48 was prepared, for instance, listing a plurality of identification units 50 spaced apart in a predetermined manner on a Mylar sheet 48. One hundred various identification units 50 were printed on the Mylar sheet 48 in a $10 \times 10$ arrangement, and then the master sheet 48 was photographically reduced from 20 to 1 reduction. Once the photographic reduction was accomplished, a negative or a positive contact was produced on which a photosensitive resist was deposited in a vacuum frame and then developed. The resist was then applied to a ceramic wafer 52 as shown in FIG. 11, the dimensions of which would be approximately at least 15 mm. square. The ceramic wafer was previously coated with a layer 44 of ni-chrome and with a superimposed gold layer 46. The resist was applied to the gold layer 46 and the whole was dipped into a suitable acid (aqua regia) for etching after which the information was positively or negatively etched on the wafer. The wafer 52 having the 100 idenification units 50 was then scored by laser equipement, and then the wafer 52 was fractured along the laser-inscribed lines, fracturing the wafer at least into 100 small chips or carriers 10 each having the identification information 50 inscribed thereon.

The carrier, of course, could be made in many different forms and procedures. For instance, the carrier could be of a stainless steel ribbon on which the information is directly inscribed by engraving procedures. The process described above is the best and most economical which has been considered to date. It should also be mentioned that the information can be etched directly through the gold layer 46 into the ni-chrome steel layer 44, or the gold can be etched away leaving only the information as the layer 46 on the metal layer 44. Because of vacuum-depositing procedures, it is also believed that the ni-chrome layer could be dispensed with and the gold layer could be adhered directly to the ceramic substrate.

Figure 8:
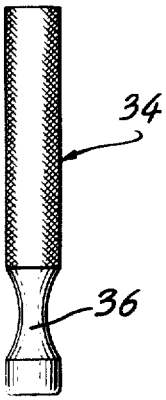
FIG. 8 is an enlarged view of a detail of FIG. 5.
Figure 9:
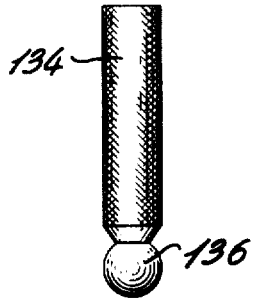
FIG. 9 is an enlarged view, similar to FIG. 8, but showing a further embodiment thereof.

If it is necessary to use a locating pin, such as shown in FIGS. 2, 4, 5, 8 and 9, it will be important that the tip 36, 136 of the pin 34, 134 be shaped to distinguish it from commonly used cylindrical pins used for anchoring crowns and such in dental restoration. FIGS. 8 and 9 show two different types of terminal shapes 36, 136 which could be used to distinguish the pin 34, 134 as a locating pin when viewed radiographically. Preferably, the pin 34, 134 would be 3 mm long and would have a diameter of approximately 0.685 mm.

Figure 5:
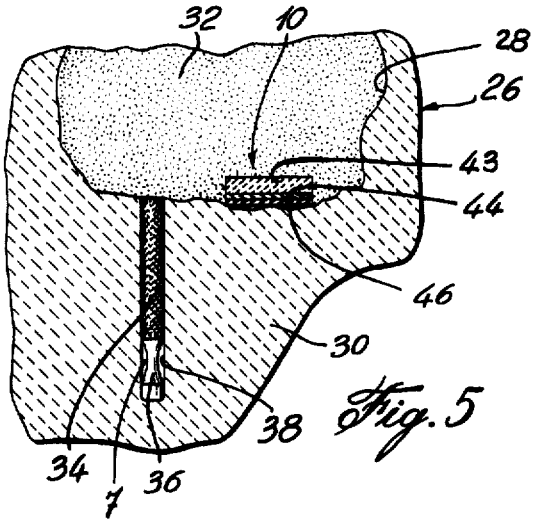
FIG. 5 is an enlarged fragmentary view of a detail of a further embodiment of the present invention.

Referring to FIG. 5, when a locating pin 34 is being used, a further cavity is bored communicating with the main restoration cavity and a pin 34 having a terminal end 36 is inserted therein. The cavity 38 could be of a dimension slightly smaller than the pin 36 whereby the pin could be forced therein because of the resiliency of the dentin 30 of the tooth 26. The cavity 38 could also be made slightly larger and provided with a translucent cement compound to fill the voids.

The method of installing carrier 10 in a tooth as shown in FIGS. 2 and 5 is as follows.

A tooth 26 is selected and a cavity 28 about 4 mm deep and about 2 mm square in cross-section is made. Slightly toward the rear of the tooth 26, away from the pulp chamber 40, there is formed a bored cavity 7 which is about 4 mm deep and is just large enough to receive pin 34 or 134. The next step, therefore, involves the introduction of pin 9 into cavity 7. After the pin has been introduced and solidified, the carrier 10 is placed in the cavity 28, face down. A varnish, sealer or adhesive may be placed over the carrier 10. This is allowed to dry, and the amalgam 32 is placed over it, it is carved and finally checked for occlusions.

It is preferable to verify that the process has been carried out satisfactorily and for this purpose, the tooth provided with an identification tab is X-rayed. The result should be comparable to FIG. 4 of the drawings, which will show the pin 34 and possibly carrier 10.

The pathologist, in trying to identify the victim, will first X-ray the teeth. If the carrier 10 is presently in the teeth, either it or the pin 34 will shown up in the radiograph. Then an excavation of the filling in that tooth is made to obtain the carrier, or the tooth may be removed from the corps, incinerated and the carrier recovered, and then the information can be read therefrom under magnification.

I claim:

1. An identification means adapted for use in living bodies and more particularly to be embedded in a cavity in a highly mineralized portion of the body comprising a carrier made up of a substrate of relatively hard inert material having a high melting point at least as high as the highly mineralized portion of the body into which it is to be embedded; an etchable layer of an inert material on said substrate and including identifying intelligence etched thereon, said identification means including locating means.

2. An identification means as defined in claim 1 wherein the locating means includes providing the carrier with a distinctive shape enabling radiographical detection of the carrier.

3. An identification means as defined in claim 1 wherein the carrier has a flat surface on which the identifying information is inscribed, said surface being 1.1 $mm^2$ and 2.5 $mm^2$, and having a thickness in the range of 0.250 mm and 1.270 mm.

4. An identification means as defined in claim 3, wherein the carrier is prismatic, being 1.5 mm square and 0.6 mm thick.

5. An identification means as defined in claim 1, wherein the inert material is chosen from the group of materials containing ceramic, porcelain, non-oxidizing metals having a melting point higher than 1250° F.

6. An identification means as defined in claim 1, wherein the inert material is a ceramic made from the group including BeO and $Al_2O_3$.

7. An identification means as defined in claim 6, wherein the carrier has a layer of ni-chrome steel deposited on the ceramic substrate.

8. An identification means as defined in claim 7, wherein a gold layer superimposes the ni-chrome steel layer and the identifying information is etched on the gold layer.

9. An identification means as defined in claim 6, wherein a gold layer is deposited on the ceramic substrate and the identifying intelligence is etched on the gold layer.

10. A method for providing positive identification of a living body comprising:

a. providing a hard, highly mineralized portion of the body with a cavity, b. placing identifying intelligence on a radiographically detectable carrier, c. embedding the carrier in the cavity whereby the carrier is completely within the mineralized portion of the body such as to lend a high degree of heat and impact protection to the carrier.

11. An identification means as defined in claim 1 wherein the carrier includes a substrate of relatively inert material and includes at least one layer of metallic material on the substrate on which identifying intelligence is etched.

[12. An identification means as defined in claim 11 including locating means for enabling the radiographical detection of the carrier, the locating means comprising a cylindrical pin of inert material having an end of the cylindrical pin being formed in a predetermined detectable shape.]

13. An identification means as defined in claim [12] *28* wherein the pin is of stainless steel material and is approximately 3 mm in length and 0.685 mm in diameter.

14. A method for positive identification of a living person, including the steps of selecting a carrier of relatively inert material and of miniaturized dimensions, applying identification intelligence corresponding to the person on said carrier, selecting a tooth of the person and excavating a suitable cavity in said tooth, locating said miniaturized carrier in the cavity formed in said tooth, closing said cavity, ensuring that the carrier is detectable radigraphically; in subsequent necessity of identification taking an X-ray of the person's teeth, detecting the carrier by X-ray and locating the tooth in which the carrier is embedded, retrieving the carrier from said tooth and reading the identifying information from the carrier.

15. A method as defined in claim 14, wherein an additional cavity is provided in the tooth suitable to receive a locating pin, selecting a relatively inert, radiographically opaque locating pin and inserting it into the additional cavity in order to enhance the detection of the tooth bearing the carrier.

16. A method as defined in claim 15, including the further step of shaping an end of said pin in a predetermined manner in order to enhance the detection thereof.

17. A method in accordance with claim 10 wherein the living body is that of a human being, and a miniaturized carrier is selected.

18. A method as defined in claim 10 wherein the highly mineralized tissue portion of the body is a tooth and the carrier is miniaturized and embedded in the tooth.

19. A method as defined in claim 10 wherein the highly mineralized portion of the body is a bone and the carrier is embedded in the bone and the bone is allowed to heal over the carrier.

20. A method as defined in claim 19 wherein the bone is the mandible bone.

21. A method as defined in claim 10 wherein the living body is that of a human being and a miniaturized carrier is is selected, the carrier being of relatively inert material and the highly mineralized portion is the mandible bone of the human body.

22. A method as defined in claim 21 wherein a radiographically opaque locating means is provided near the carrier to enable radiographic detection of the carrier.

23. A method as defined in claim 22 wherein the locating means includes a pin in the form of an elongated member and shaping the end of said pin in a predetermined manner in order to enhance the detection thereof.

24. The method of claim 10 wherein said carrier is formed by a. forming a substrate of relatively inert material,
b. depositing at least one layer of metallic material on said substrate,
c. etching the identifying intelligence in said metallic material.

25. A method for providing positive identification of a living body comprising:

a. forming a cavity in a tooth of the living body,
b. placing identifying intelligence on a radiographically detectable carrier,
c. inserting the carrier in the cavity of the tooth,
d. covering the carrier within the cavity.

26. The method of claim 24 including inserting a radiographically opaque locating means in the tooth adjacent said carrier.

27. The method of claim 26 wherein said locating means in inserted by forming an elongated cavity adjacent the cavity containing said carrier and placing said locating means in the form of an elongated member in said elongated cavity.

*28. An identification means adapted for use in living bodies and more particularly to be embedded in a cavity in a highly mineralized portion of the body comprising a carrier made up of a substrate of relatively hard inert material having a high melting point at least as high as the highly mineralized portion of the body into which it is to be embedded; and inscribable layer of an inert material on said substrate and including identifying intelligence inscribed thereon, said identification means including locating means for enabling the radiographical detection of the carrier, the locating means comprising a cylindrical pin of inert material having an end of the cylindrical pin being formed in a predetermined detectable shape.*

* * * * *